United States Patent [19]
Edwards et al.

[11] 4,308,402
[45] Dec. 29, 1981

[54] PROCESS FOR METHYL-CAPPED ALKOXYLATES

[75] Inventors: Charles L. Edwards; Andrea Sanders; Lynn H. Slaugh, all of Houston, Tex.

[73] Assignee: Shell Oil Company, Houston, Tex.

[21] Appl. No.: 96,122

[22] Filed: Nov. 20, 1979

[51] Int. Cl.³ .............................................. C07C 43/11
[52] U.S. Cl. ................................... 568/618; 252/457; 252/458; 252/468; 252/469
[58] Field of Search ......................................... 568/618

[56] References Cited

FOREIGN PATENT DOCUMENTS 49-25246  6/1974  Japan .

Primary Examiner—Paul J. Killos

[57] ABSTRACT

A terminal —CH₂OH moiety is selectively cleaved from an alkoxyalkanol at elevated temperatures, in the optional presence of water, over a catalytically effective amount of heterogeneous nickel.

11 Claims, No Drawings

PROCESS FOR METHYL-CAPPED ALKOXYLATES

BACKGROUND OF THE INVENTION

This invention relates to a process for the treatment of alkoxyalkanols. More particularly, this invention is directed toward a process for the cleavage of a terminal —$CH_2OH$ moiety from an alkoxyalkanol at elevated temperatures in the presence of a catalytically effective amount of heterogeneous nickel. The resulting compounds are referred to herein as methyl-capped alkoxylates.

Methyl-capped alkoxylates find use as solvents or as low foam detergents for industrial applications. Since these detergents are composed only of the elements carbon, hydrogen and oxygen, they do not pose the environmental problems which stem from detergents containing such heteroatoms as nitrogen, sulfur or phosphorus. However, in the production of the methyl-capped alkoxylates, the ether linkages in the alkoxyalkanol starting materials degrade easily at elevated temperatures; a mild, selective process for production of the methyl-capped alkoxylates is thus of commercial interest.

Rylander, "Organic Synthetic with Noble Metal Catalysts," (1973) discloses on page 269 the dehydrogenation and decarbonylation of primary alcohols upon heating with a catalyst. There appears no disclosure of nickel catalysts or alkoxylated alcohols however.

U.S. Pat. No. 3,894,107 discloses the conversion of alcohols to hydrocarbons over a zeolite catalyst impregnated with a metal cation from Groups I-VIII. U.S. Pat. No. 3,920,766 teaches the conversion by simultaneous dehydration and hydrogenation of t-butanol to isobutane over a supported nickel catalyst. Neither of these patents disclose a process which yields a product with one less carbon atom than the reactant alcohol.

U.S. Pat. No. 3,501,546 discloses the conversion of alcohols with n carbon atoms to hydrocarbons with (n-1) and (2n-1) carbon atoms over a palladium on titanium dioxide catalyst. The presence of water is said to favor products with (2n-1) carbon atoms.

U.S. Pat. No. 4,139,496 teaches the steam dealkylation of alkyl-aromatic hydrocarbons over a supported alumina catalyst containing oxides of nickel, potassium and chromium, with at least a portion of the nickel being in the form of free metal.

Badin, *Journal of the American Chemical Society*, Vol. 65, pages 1809-13 (1943), shows the liquid phase conversion of primary aliphatic alcohols into the corresponding aldehyde, an unsaturated hydrocarbon of one less carbon atom and the saturated hydrocarbon of one less carbon atom. The catalyst employed was Raney nickel.

SUMMARY OF THE INVENTION

A process has now been discovered for cleaving a terminal —$CH_2OH$ moiety from an alkoxyalkanol of the formula:

$$RO(CH_2CHR'O)_nCH_2CH_2OH \quad (I)$$

wherein n is an integer of from 1 to 12, R is an alkyl group of 1 to 22 carbon atoms and R' is hydrogen or methyl, with the proviso that when n is an integer of greater than 1, R' may represent mixtures of hydrogen and methyl. The process comprises reacting an alkoxyalkanol of formula (I) at elevated temperatures in the presence of a catalytically effective amount of heterogeneous nickel. The process converts the alkoxyalkanol with high selectivity and yield, and substantially without thermal degradation of the ether linkages, to a methyl-capped alkoxylate of the formula:

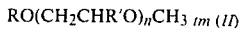

wherein R, R' and n have the same meanings as above.

DESCRIPTION OF THE PREFERRED EMBODIMENTS

Preferred alkoxyalkanol reactants of formula (I) above are compounds wherein R is alkyl of 9 to 22 carbon atoms, more preferably 12 to 15 carbon atoms, R' is hydrogen or methyl, more preferably hydrogen, and n is an integer of from 1 to 12, more preferably from 2 to 9, and most preferably from 3 to 6. Thus, the most preferred alkoxyalkanol reactant corresponds to formula (I) wherein R is alkyl of 12 to 15 carbon atoms, R' is hydrogen and n is an integer from 3 to 6. The R group may be optionally substituted with any substituent which does not interfere with the cleavage of the terminal $CH_2OH$ moiety, e.g. —OR", —$CH_3$ and —C(O)$NH_2$, wherein R" represents an alkyl or aryl group of up to 20 carbon atoms. However, compounds where R is unsubstituted are preferred. The R' group can be hydrogen or methyl with the proviso that when n is an integer of greater than one, R' may represent mixtures of hydrogen and methyl. For example, straight ethoxylates, straight propoxylates or mixed ethoxylate-propoxylate detergent alcohols are commercially available. The process is particularly suited to the detergent range ethoxylated or propoxylated alcohols with the alkyl chains (R) preferred above of 9 to 22 carbon atoms. Detergent range ethoxylated alcohols are commercially available in which the number (n) of ethoxylate groups ($CH_2CHR'O$, with R'=H) is an average of 2.25, 3, 5, 6.5, 7, 9, 11, 12 or 13 groups per molecule. Others may be readily prepared by methods known in the art, such as the reaction of a detergent range alcohol with ethylene oxide in the presence of a base. The reactants should not contain impurities which would poison the nickel catalyst.

Although the process is more suited to the preparation of compounds with utility in the field of detergents, it may also be directed to the production of ethereal solvents. For such solvent applications, preferred alkoxyalkanol reactants are of formula (I) above, wherein R is alkyl of 1 to 8 carbon atoms, more preferably one to two carbon atoms, R' is hydrogen or methyl, more preferably hydrogen, and n is an integer from 1 to 4, more preferably the integer one. Thus, the most preferred alkoxyalkanol reactant when a product useful as a solvent is desired corresponds to formula (I) wherein R is methyl, R' is hydrogen and n is one, commonly known as methyl carbitol. The methyl-capped alkoxylate product from this preferred reactant is glyme, or 1,2-dimethoxyethane.

The reaction is carried out at elevated temperatures. For products having detergent applications, temperatures of from about 150° to 270° C. are preferred, with 200° to 250° C. more preferred and 225° to 250° C. most preferred. For products having solvent applications, temperatures of from about 150° C. to about 250° C. are preferred, with 180° C. to 250° C. more preferred. The fixed bed reaction vessel is suitably heated to the desired temperature. As a general proposition, higher temperatures may increase the percent conversion of the alkoxyalkanol reactant, but also serve to reduce selectively and increase unwanted side reactions. In no case should a temperature be used which substantially degrades the ether linkages of the reactant or the methyl-capped alkoxylate product.

The process is optionally and preferably carried out in the presence of water. The amount of water added may vary widely; preferably, it may vary from about 15 to about 50 percent by volume of the reactant feed. The water may be mixed with the alkoxyalkanol feedstock if the resulting mixture is homogeneous or, particularly in cases where larger volumes of water (i.e. 50% or more) are used and/or gel formation occurs, the water may be separately pumped directly into the reaction vessel. The presence of water generally improves the selectivity and/or activity of the catalyst used in the process.

The catalyst utilized is heterogeneous nickel metal, either the metal alone or, more preferably, supported on an inert refractory support with a surface area of at least 1 square meter per gram. At least some, and more preferably substantially all, of the nickel must be in its reduced (metallic) state prior to use in the process. A wide variety of such supported and unsupported nickel catalysts are commercially available and their preparation is described in the art relating to such areas as oligomerization or hydrogenation. Prior to use in the process of this invention, the commercially obtained catalysts are suitably treated and/or activated with hydrogen according to the manufacturer's specifications. Catalysts otherwise prepared are reduced in a conventional manner; the supported catalysts are generally calcined with air and reduced at elevated temperatures with hydrogen prior to use. Thus, at least in the case of a supported catalyst, the portion, if any, of the nickel not present in its reduced (metallic) state will generally be present in its oxide form.

A variety of nickel-containing compounds may be used to deposit the nickel on the support, with those in which the nickel is more readily reduced being preferred. Examples of suitable water soluble nickel-containing compounds include nickel nitrate, nickel sulfate and nickel acetate, with nickel nitrate being preferred. The use of nickel halides or sulfides, especially nickel fluoride, is to be avoided since such compounds are more difficult to reduce and are believed, in some cases, to affect the support or deactivate the catalyst. Although the water soluble nickel-containing compounds are preferred in connection with the supported catalysts for reasons of economy and convenience, other nickel-containing compounds may be used. For example, organonickel compounds such as nickel tetracarbonyl may be employed and are deposited on the support using a suitable solvent, e.g. toluene. In the case of a supported catalyst, there may optionally be metal(s) other than nickel deposited on the support; among such other metal(s), chromium and/or zinc are preferred. The use of such additional metal(s) is preferred in the preparation of products useful as solvents, e.g. glyme. Thus, a Ni/Cr/Zn supported catalyst is preferred for the preparation of glyme from methyl carbitol. However, in all cases, the use of any additional metal(s) which deactivate the catalyst is to be avoided. Amounts of nickel present on the support are not critical, although amounts from about 5 to about 70 weight-percent (wt-%) of nickel are preferred. The commercially obtained catalysts commonly contain from about 40 to about 70 wt-% nickel. Catalysts otherwise prepared, such as nickel on various aluminas, typically contain from about 5 to about 15 wt-% nickel. Supported catalysts wherein metal(s) other than nickel are additionally present typically contain nickel loadings of 10 wt-% or less; the amount(s) of additional metal(s) are again not critical, but are typically each present in amounts less than about 6 wt-%.

In the supported catalysts, the nickel is deposited on a suitable inert refractory support with a surface area of at least 1 square meters per gram. Supports with moderate surface areas have been found to result in higher catalyst selectivity and/or activity. Although preferred surface areas may vary depending on the nickel loading to be deposited on the support, in general those supports with surface areas from about 9 to about 270 square meters per gram ($m^2/g$) are preferred, with about 9 to about 160 $m^2/g$ more preferred, and about 59 to about 135 $m^2/g$ most preferred. Thus, a catalyst prepared on an alpha-alumina support with a surface area of 0.2 $m^2/g$ is essentially inactive in the process. Highly acidic supports (e.g. MSA-3, a silica-alumina type support) are believed to have an adverse effect on the selectivity of the process; their use should therefore be avoided. Within these limits, the support chosen is not critical and a wide variety of materials may be employed, many of which are commercially available. Examples of suitable supports include moderate surface area aluminas, silicas, kieselguhr, aluminosilicates which are not highly acidic and activated carbon. Examples of commercially available supported nickel catalysts, with the surface area of the support in $m^2/g$ following in parentheses, include Harshaw 1404T (125), Gridler G87RS (46) and Calsicat E-230T (160). The support in all cases should be inert to the reaction conditions.

In the cases where an unsupported nickel catalyst is used, the surface area should again be at least 1 square meter per gram, with surface areas from about 100 to about 270 $m^2/g$ preferred. The preferred unsupported catalyst is Raney nickel.

The reaction may be carried out batchwise or continuously, with the continuous process being preferred. The reaction takes place in one or more reaction tubes, with a fixed bed reactor system being preferred. If a plurality of reaction tubes are employed, they may be arranged in parallel or in series; if a series of tubes are employed, means of heating or cooling the reaction tubes are suitably incorporated between said tubes. If desired, the catalyst may be regenerated in a conventional manner; the reaction tube(s) will then incorporate means of facilitating the regeneration. The reaction is preferably carried out in the presence of a hydrogen flow to stabilize the catalyst and maintain at least some, more preferably substantially all, of the nickel in its reduced (metallic) state during the reaction. Thus, the process is suitably carried out in a stainless steel hot tube reactor in the presence of a continuous hydrogen flow (e.g., approximately 0.1 liters to 10 liters of $H_2$ per hour per 5 grams of catalyst) to stabilize and maintain the activity of the catalyst. For example, in a continuous process the reactant alkoxyalkanols, optionally and preferably in the presence of water, are typically passed through the reaction tube containing the catalyst bed at a liquid hourly space velocity (LHSV) from 0.1 to 5. [LHSV = (volume of reactant injected/volume of catalyst)/hours]. If a single pass through the reactor system does not yield the desired degree of reaction, the material can be recycled to obtain a higher conversion to product, or in the case of a plurality of reaction tubes arranged in a series, passed through subsequent reaction tube(s). If desired, the lighter products with utilities as ethereal solvents may be further purified by distillation.

The following factors, among others, therefore determine the selectivity and activity of the catalyst and process herein: reaction temperature, optional presence or amount of water, the reactant alkoxyalkanol chosen, amount of the nickel catalyst and, additionally in the case of a supported catalyst, the optional presence or amount(s) of other metal(s) in the catalyst, the type of support, the nickel loading on the support and the surface area of the support.

The desired products are methyl-capped alkoxylates of formula (II) above. Smaller amounts may also be formed of ethyl-capped alkoxylates of the formula:

$$RO(CH_2CHR'O)_nCH_2CH_3 \quad (III)$$

wherein R, R' and n have the same meanings as above. In the cases where the products will be utilized for detergent applications, it is believed that the presence of such an ethyl-capped alkoxylate is not necessarily detrimental and may in fact prove beneficial. Other by-products of the reaction may include carbon monoxide, carbon dioxide, alcohols, ethers, and hydrocarbons, as well as minor amounts of unidentified species. While applicants do not wish to be bound by any theory, the reaction is thought to proceed via the following dehydrogenation-decarbonylation scheme:

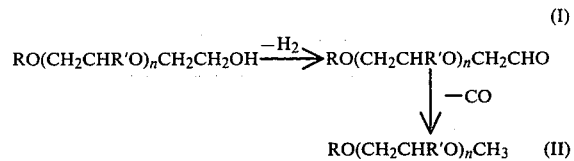

$$RO(CH_2CHR'O)_nCH_2CH_2OH \xrightarrow{-H_2} RO(CH_2CHR'O)_nCH_2CHO \quad (I)$$
$$\downarrow -CO$$
$$RO(CH_2CHR'O)_nCH_3 \quad (II)$$

With the addition of water to the reaction medium, carbon dioxide appears as a product. Again, while not wishing to be bound, the presence of water is thought by applicants to facilitate the decarbonylation reaction, thus producing $CO_2$ instead of CO.

The yields of the methyl-capped alkoxylate (II) obtained from the process of this invention are excellent with, under optimum conditions, conversion of the alkoxyalkanol (I) and molar selectivity in excess of 90% obtained.

For the conversion of detergent range alkoxyalkanols, the preferred catalyst comprises 60 to 70 wt-% nickel deposited on an inert refractory support with a surface area of 115 to 135 $m^2/g$ and preferred reaction conditions include the presence of 50% water by volume, a continuous hydrogen flow and a temperature of approximately 225° C. Harshaw 1404T is an example of this preferred catalyst which is commercially available. The reaction carried out with this combination of parameters affords both high selectivity and conversion. If lower rates of conversion are acceptable, then a catalyst comprising about 6.4 wt-% nickel on alumina with a surface area of approximately 9 $m^2/g$ affords 100% selectivity to the desired methyl-capped alkoxylate. If lower nickel loadings are desired, a catalyst comprising 6.2 wt-% nickel on alumina with a surface area of approximately 100 $m^2/g$ affords both high selectivity and conversion, with or without the presence of water, at a reaction temperature of about 250° C. and a continuous hydrogen flow. If a supported mixed metal catalyst is desired, approximately 7.2 wt-% nickel, 1.1 wt-% chromium and 4.4 wt-% zinc deposited on an alumina with a surface area from about 59 to about 100 $m^2/g$ affords both high selectivity and conversion, in the presence of 50% water by volume, a continous hydrogen flow and a temperature of 250° C. For the conversion of lower molecular weight alkoxyalkanols into a product with utility as a solvent, e.g., glyme, the aforesaid supported mixed metal catalyst is preferred, in the presence of 50% water by volume and a continuous hydrogen flow. One skilled in the art will appreciate that the selectivity and conversion to any given methyl-capped alkoxylate, including those products having solvent applications, may be further optimized through the selection of appropriate reaction parameters such as temperature, pressure and reactor design.

The invention is illustrated further in the following examples, which are not to be construed as limiting its scope. In examples where the starting alkoxyalkanol was a SHELL NEODOL® ethoxylate 23-3T, this reactant was prepared by ethoxylating a mixture of $C_{12}$ and $C_{13}$ substantially straight chain alcohols ($C_{12}:C_{13} \sim 40:60$) to an ethoxylate having an average of about 3 ethylene oxide units per molecule and then topping off the unreacted alcohols and lower ethoxylates so that the final product has an average of about five ethylene oxide units per molecule. In examples where the starting alkoxyalkanol was methyl carbitol, this reactant was obtained from Aldrich Chemical Company and purified by passing over a column of activated alumina. Plant hydrogen was used during all reactions to stabilize the catalyst and maintain the nickel in its reduced form. When required, plant distilled water was used in catalyst preparation and with the alkoxyalkanol feed.

The commercially prepared supported nickel catalysts, when used, were as follows:

Harshaw 1404T from Harshaw Chemicals (67 wt-% nickel, 125 $m^2/g$ surface area, 10×20 mesh)

Girdler G-87RS from United Catalysts, Inc. (42 wt-% nickel, 46 $m^2/g$ surface area)

Calsicat E-230T from Calsicat Division of Mallinckrodt Chemicals (58 wt-% nickel, 160 $m^2/g$ surface area).

The commercially prepared supports, when used, were as follows:

RA-1 alumina from Reynolds Company,
SCS alumina from Rhodia, Inc.,
Alpha-alumina from Norton as SA-5559,
MSA-3 silica-alumina from American Cyanamid.

The following abbreviations are used in the examples.
22-3T for NEODOL® ethoxylate 23-3T
LHSV for liquid hourly space velocity
Me-cap for the methyl-capped ethoxylate of formula (II)
Et-cap for the ethyl-capped ethoxylate of formula (III).

Furthermore, ROH and ROCH$_3$ are used to designate alkanols and alkyl ethers respectively, wherein R has the meaning as defined above (i.e. R=dodecyl or tridecyl when 23-3T is used as the reactant).

EXAMPLE I

A supported nickel/chromium/zinc catalyst was typically prepared according to the following procedure. A solution of 8.03 grams of $Ni(NO_3)_2.6H_2O$, 4.10 grams of $Zn(NO_3)_2.6H_2O$ and 1.98 grams of $Cr(NO_3)_2.9H_2O$ dissolved in 12 milliliters of water was added to 24 grams of SCS-59 alumina (dry impregnation). This material was dried in vacuo until free flowing. The solid was added to a hot tube reactor and calcined with air in increments of 100° C. from 25° C. to 500° C. over a period of 4 hours. This catalyst precursor was reduced in a stream of plant hydrogen in increments of 100° C. from 25° C. to 500° C. over 6 hours. Finally, the catalyst was reduced at 500° C. for 16 hours and used without further treatment at the desired reaction temperature. A sample of the calcined catalyst analyzed using x-ray fluorescence showed 7.3% Ni/1.2% Cr/4.5% Zn, expressed in weight-percents.

EXAMPLE II

A supported nickel catalyst was typically prepared according to the following procedure. A solution of 9.15 grams of $Ni(NO_3)_2.6H_2O$ in 15 milliliters of water was used to impregnate 30 grams of calcined alumina. The material was dried in vacuo until free flowing. This material was calcined in air to 500° C. in increments of 100° C. per 2 hour period and calcined further at 500° C. for 6 hours. The catalyst was cooled to 25° C. and then reduced using 6% hydrogen in nitrogen to 500° C. in increments of 100° C. per 2 hour period, followed by further reduction at 500° C. for 16 hours. Analysis of the catalyst by x-ray fluorescence showed a nickel content of 7.1 weight-percent.

EXAMPLE III

In a typical experiment using a NEODOL ® ethoxylate 23-3T alcohol as the reactant, 10 milliliters of a Harshaw 1404T catalyst were added to a stainless steel vertical hot tube reactor. The catalyst was activated by treatment with hydrogen gas at 225° C. for 16 hours. NEODOL ® ethoxylate 23-3T was introduced at a rate of about 5 milliliters per hour (LHSV=0.5) while a hydrogen flow of approximately 10 liters per hour was continued. In examples where water is shown to be present, it was mixed with the reactant feed or, especially in cases of larger amounts of water, pumped separately over the catalyst bed to avoid gel formation; water remaining in the product stream was stripped before analysis of products. For example, an 85% 23-T:15% water (by volume) solution was charged to the reaction tube at about 5 milliliters per hour (LHSV=0.5) when indicated. In examples with 50% by volume of water in the feed, the 23-3T and water were separately charged to the reaction tube, each at about 5 milliliters per hour (LHSV=0.5 based on 23-3T feed only).

The product stream passed through a Grove ® regulator into a liquid sample collector and hourly samples were taken. The samples were analyzed by $C^{13}$ nuclear magnetic resonance spectroscopy. For subsequent runs, the feedstock flow was stopped, the reactor cooled to 25° C. under hydrogen for 16 hours and finally heated up to the desired temperature (e.g. 225° C.) prior to reaction.

Several parameters were varied and the results are shown in Table I. Example III-3 shows high conversion and selectivity to the desired methyl-capped ethoxylate when 50% by volume of water was added with the reactant. Examples III-9 and III-10 show 100% molar selectivity to the methyl-capped ethoxylate, albeit at lower levels of conversion.

TABLE I

Nickel Catalyzed Conversion of NEODOL ® Ethoxylate 23-3T to Methyl-Capped Ethoxylate

| Example No. | Catalyst | Temp. (°C.) | Surface Area (m²/g) | % H₂O (by volume) in feed[a] | Conv. (%) | % Molar Selectivities | | | | |
|---|---|---|---|---|---|---|---|---|---|---|
| | | | | | | Me—Cap | Et—Cap | ROH | ROCH₃ | Other |
| III-1 | 67% Ni Harshaw 1404T | 225 | 125 | 0 | 43 | 95 | | 5 | | |
| III-2 | 67% Ni Harshaw 1404T | 225 | 125 | 15 | 65 | 97 | | 3 | | |
| III-3 | 67% Ni Harshaw 1404T | 226 | 125 | 50 | 90 | 94 | 3 | 3 | | |
| III-4 | 7.1% Ni/RA-1 Al₂O₃ | 225 | 263 | 0 | 16 | 50 | 12 | 18 | | 20 |
| III-5 | 7.1% Ni/RA-1 Al₂O₃ | 225 | 263 | 15 | 15 | 80 | | 13 | | 7 |
| III-6 | 7.1% Ni/RA-1 Al₂O₃ | 250 | 263 | 0 | 48 | 54 | 10 | 6 | | 30 |
| III-7 | 7.1% Ni/RA-1 Al₂O₃ | 250 | 263 | 15 | 50 | 74 | 10 | 6 | | 10 |
| III-8 | 15.1% Ni/RA-1 Al₂O₃ | 226 | 263 | 0 | 42 | 71 | 14 | 2 | | 12 |
| III-9 | 42% Ni Girdler G-87RS | 225 | 46 | 0 | 23 | 100 | | | | |
| III-10 | 42% Ni Girdler G-87RS | 225 | 46 | 15 | 27 | 100 | | | | |
| III-11 | 58% Ni Calsicat E-230T | 225 | 160 | 0 | 59 | 93 | 7 | | | |
| III-12 | 58% Ni Calsicat E-230T | 225 | 160 | 15 | 56 | 96 | 4 | | | |
| III-13 | 58% Ni Calsicat E-230T | 250 | 160 | 0 | 95 | 72 | 14 | | 14 | |
| III-14 | 58% Ni Calsicat E-230T | 250 | 160 | 15 | 96 | 75 | 14 | | 11 | |

[a]LHSV was approximately 0.5.

EXAMPLE IV

Experiments were run according to the general procedure of Example III. Several parameters were varied and the results are shown in Table II. The examples show the generally beneficial effects of using alumina supports with moderate surface areas, at the specified nickel loadings, as well as effects of increased reaction temperatures and the presence of water. Examples IV-10 shows that alpha-alumina, a low surface area support is essentially inactive with the specified nickel loading of 6.7 wt-%. Examples IV-11 and IV-12 show the reduced selectivity obtained with nickel fluoride deposited on a support with a high surface area (MSA-3).

TABLE II

Nickel Catalyzed Conversion of NEODOL ® Ethoxylate 23-3T to Methyl-Capped Ethoxylate

| Example No. | Catalyst | Temp. (°C.) | Surface Area (m²/g) | % H₂O (by volume) in feed[a] | Conv. (%) | % Molar Selectivities |||||
|---|---|---|---|---|---|---|---|---|---|---|
| | | | | | | Me—Cap | Et—Cap | ROH | ROCH₃ | Other |
| IV-1 | 6.2% Ni/SCS-100 | 225 | 100 | 0 | 32 | 88 | 3 | 6 | | 3 |
| IV-2 | 6.2% Ni/SCS-100 | 250 | 100 | 0 | 86 | 81 | 9 | | 6 | 4 |
| IV-3 | 6.2% Ni/SCS-100 | 250 | 100 | 50 | 97 | 78 | 14 | | 8 | |
| IV-4 | 7.1% Ni/SCS-59 | 225 | 59 | 0 | 32 | 87 | 6 | | | 7 |
| IV-5 | 7.1% Ni/SCS-59 | 225 | 59 | 15 | 42 | 90 | 3 | | | 7 |
| IV-6 | 6.4% Ni/SCS-9 | 225 | 9 | 0 | 24 | 100 | | | | |
| IV-7 | 6.4% Ni/SCS-9 | 225 | 9 | 15 | 41 | 100 | | | | |
| IV-8 | 6.4% Ni/SCS-9 | 250 | 9 | 0 | 70 | 87 | | 4 | | 9 |
| IV-9 | 6.4% Ni/SCS-9 | 250 | 9 | 15 | 80 | 89 | 5 | 3 | | 3 |
| IV-10 | 6.7% Ni/alpha-alumina | 225 | 0.2 | 0 | <1 | — | | | | |
| IV-11 | NiF₂/MSA-3 | 224 | 325 | 0 | 16 | 13 | 13 | 25 | | 51 |
| IV-12 | NiF₂/MSA-3 | 250 | 325 | 0 | 50 | 18 | 16 | 16 | | 50 |

[a]LHSV was approximately 0.5.

EXAMPLE V

Experiments were again run according to the general procedure of Example III, with variation of several parameters. The results are shown in Table III. The examples show the effect of using supported nickel/chromium/zinc catalysts. Examples V-2 and V-6 show both high conversion and selectivity to the desired methyl-capped product. Example V-7 shows the poor performance of the catalyst when deposited on a higher surface area support.

TABLE III

Effect of Ni/Cr/Zn Catalysts Supported on Aluminas on Methyl-Capped NEODOL ® Ethoxylate Production

| Example No. | Catalyst[a] | Temp. (°C.) | Surface Area (m²/g) | % H₂O (by volume) in feed[b] | Conv. (%) | % Molar Selectivities |||||
|---|---|---|---|---|---|---|---|---|---|---|
| | | | | | | Me—Cap | Et—Cap | ROH | ROCH₃ | Other |
| V-1 | A | 250 | 59 | 0 | 22 | 73 | 14 | 0 | 0 | 13 |
| V-2 | A | 250 | 59 | 50 | 80 | 89 | 10 | 0 | 0 | 1 |
| V-3 | B | 250 | 59 | 0 | 28 | 71 | 0 | 0 | 0 | 28 |
| V-4 | B | 250 | 59 | 15 | 58 | 86 | 10 | 4 | 0 | 0 |
| V-5 | C | 225 | 100 | 50 | 43 | 81 | 14 | 5 | 0 | 0 |
| V-6 | C | 250 | 100 | 50 | 92 | 80 | 18 | 0 | 0 | 2 |
| V-7 | D | 240 | 263 | 0 | 9 | 33 | 0 | 67 | 0 | 0 |

[a]Catalyst A = 7.3% Ni/1.2% Cr/4.5% Zn/SCS-59
Catalyst B = 7.0% Ni/1.2% Cr/4.1% Zn/SCS-59
Catalyst C = 7.1% Ni/1.0% Cr/4.3% Zn/SCS-100
Catalyst D = 6.1% Ni/0.9% Cr/4.5% Zn/RA-1
[b]LHSV = 0.5 based on 23-3T feedstock

EXAMPLE VI

In a typical experiment using methyl carbitol as the reactant, 10 milliliters (6.6 grams) of a catalyst prepared as in Example I was loaded into a stainless steel hot tube reactor and reduced in increments to 500° C. using plant hydrogen. The reactor was cooled to the desired temperature (225° C.), and a 50% aqueous solution of methyl carbitol (by volume) was added over the catalyst at 10 milliliters/hour (LHSV=0.5 based on methyl carbitol) under a hydrogen flow. An hourly liquid sample was taken and analyzed by gas-liquid chromatography using a flame ionization detector. In addition, a representative gas sample was collected and analyzed by mass spectrometry to quantify light components. Several parameters were varied and the results are shown in Table IV.

Examples VI-6 and VI-7 show good conversion rates of the methyl carbitol reactant, although Example VI-5, run at a lower temperature, shows higher selectivity to the desired glyme product.

TABLE IV

Nickel Catalyzed Conversion of Methyl Carbitol to Glyme

| Example No. | Catalyst | Temp. (°C.) | Surface Area (m²/g) | % H₂O (by volume) in Feed[a] | Conv. (%)[b] | Selectivity[c] to Glyme (adjusted) |
|---|---|---|---|---|---|---|

TABLE IV-continued

| Example No. | Catalyst | Temp | | | | |
|---|---|---|---|---|---|---|
| VI-1 | 7.1% Ni/SCS-59 | 205 | 59 | 0 | 19.4 | 40.0 |
| VI-2 | 7.1% Ni/SCS-59 | 202 | 59 | 50 | 23.6 | 46.8 |
| VI-3 | 7.1% Ni/SCS-59 | 225 | 59 | 50 | 73.2 | 0.2 |
| VI-4 | 7.3% Ni/1.2% Cr/ 4.5% Zn on SCS-59 | 202 | 59 | 50 | 13.5 | 41.3 |
| VI-5 | 7.3% Ni/1.2% Cr/ 4.5% Zn on SCS-59 | 225 | 59 | 50 | 51.2 | 62.0 |
| VI-6 | 7.3% Ni/1.2% Cr/ 4.5% Zn on SCS-59 | 249 | 59 | 50 | 88.4 | 50.0 |
| VI-7 | 7.3% Ni/1.2% Cr/ 4.5% Zn on SCS-59 | 262 | 59 | 50 | >99 | 47.9 |
| VI-8 | 67% Ni Harshaw 1404T | 203 | 125 | 0 | 27.5 | 43.0 |
| VI-9 | 67% Ni Harshaw 1404T | 204 | 125 | 15 | 20.3 | 36.7 |

| | | | Weight % Selectivities to Products | | | |
|---|---|---|---|---|---|---|
| Example No. | Glyme | Methoxy- ethanol | CO | Hydro- carbons[d] | $CH_3OCH_2CH_3$ | Other Gases |
| VI-1 | 30.0 | 11.1 | 18.6 | 6.1 | 26.4 | 4.3 |
| VI-2 | 34.6 | 9.3 | 19.2 | 6.1 | 20.0 | 4.0 |
| VI-3 | 30.3 | 13.0 | 28.0 | 4.7 | 15.0 | 2.5 |
| VI-4 | 31.0 | 3.4 | 35.9 | 1.4 | 14.6 | 9.6 |
| VI-5 | 46.5 | 6.2 | 24.4 | 2.1 | 13.0 | 7.3 |
| VI-6 | 37.5 | 6.4 | 28.4 | 2.7 | 16.5 | 7.2 |
| VI-7 | 36.2 | 3.2 | 31.8 | 3.5 | 16.2 | 7.3 |
| VI-8 | 32.0 | 20.7 | 9.3 | 10.3 | 17.8 | 3.8 |
| VI-9 | 27.5 | 17.4 | 16.3 | 9.9 | 19.4 | 4.5 |

[a] LHSV was approximately 0.5 based on methyl carbitol.
[b] Based on total weight recovered
[c] Adjusted % selectivity = $\frac{\text{wt. glyme produced}}{\text{wt. methyl carbitol converted} \times 0.75}$ = $\frac{\text{wt. glyme produced}}{\text{wt. of glyme expected}}$
[d] Includes methane, ethane and/or propane
[e] Includes carbon dioxide, hydrogen, dimethyl ether and unknown gases and liquids. Actual weight of $H_2$ produced is not known as a large $H_2$ flow (6-8 liters/hour) was used to maintain catalyst activity.

What is claimed is:

1. In a process for cleaving a terminal —$CH_2OH$ moiety from alkoxyalkanols which comprises reacting an alkoxyalkanol of the formula:

$$RO(CH_2CHR'O)_nCH_2CH_2OH$$

wherein n is an integer from 1 to 12, R is an alkyl group and R' is hydrogen or methyl with the proviso that when n is an integer of greater than 1, R' may represent mixtures of hydrogen and methyl, at a temperature of from about 150° to about 270° C. in the presence of a catalytically effective amount of a nickel-containing compound deposited on an inert refractory support, thereby affording a methyl-capped alkoxylate of the formula:

$$RO(CH_2CHR'O)_nCH_3$$

wherein n, R and R' have the same meanings as above, the improvement which comprises reacting an alkoxyalkanol in which the alkyl group R has 9 to 22 carbon atoms, in the presence of a catalytically effective amount of a reduced nickel-containing compound deposited on an inert refractory support having a surface area of from 9 to 160 square meters per gram.

2. The process according to claim 1, wherein substantially all of the nickel present is in its reduced (metallic) form.

3. The process according to claim 1, wherein R is alkyl of 12 to 15 carbon atoms and n is an integer from 3 to 6.

4. The process according to claim 3, wherein said catalyst comprises 60 to 70 weight-percent of nickel deposited on an inert refractory support with a surface area of 115 to 135 square meters per gram.

5. The process according to claim 1, wherein said nickel containing compound is nickel nitrate.

6. The process according to claim 1, wherein the catalyst additionally contains zinc and chromium.

7. The process according to claim 1, wherein the reaction is additionally carried out in the presence of a hydrogen flow sufficient to stabilize the catalyst and maintain the nickel in its reduced (metallic) form.

8. The process according to claim 1, wherein the inert refractory support comprises alumina.

9. In a process for cleaving a terminal —$CH_2OH$ moiety from alkoxyalkanols which comprises reacting an alkoxyalkanol of the formula:

$$RO(CH_2CHR'O)_nCH_2CH_2OH$$

wherein N is an integer from 1 to 12, R is an alkyl group and R' is hydrogen or methyl with the proviso that when n is an integer of greater than 1, R' may represent mixtures of hydrogen and methyl, at a temperature of from about 150° to about 270° C., in the presence of a catalytically effective amount of a nickel-containing compound deposited on an inert refractory support, thereby affording a methyl-capped alkoxylate of the formula:

$$RO(CH_2CHR'O)_nCH_3$$

wherein n, R and R' have the same meanings as above, the improvement which comprises reacting an alkoxyalkanol in which the alkyl group R has 9 to 22 carbon atoms, in the presence of up to about 50% water by volume in the reactant feed and in the presence of a catalytically effective amount of a reduced nickel-containing compound deposed on an inert refractory support having a surface area of from 9 to 160 square meters per gram.

10. The process according to claim 9, wherein substantially all of the nickel present is in its reduced (metallic) form.

11. The process according to claim 10, wherein R is alkyl of 12 to 15 carbon atoms, n is an integer of from 3 to 6 and said catalyst comprises 60 to 70 weight-percent of nickel deposited on an inert refractory support with a surface area of 115 to 135 square meters per gram.

* * * * *